United States Patent [19]

Kruse et al.

[11] 3,963,789

[45] June 15, 1976

[54] POLYHYDRIC ALCOHOL PRODUCTION USING RU ON CLAY SUPPORTS

[76] Inventors: Walter M. Kruse, 1 Woodbury Court; Leon W. Wright, 215 Oakwood Road, both of Wilmington, Del. 19803

[22] Filed: Dec. 12, 1974

[21] Appl. No.: 531,972

[52] U.S. Cl. .................... 260/635 C; 252/455 R
[51] Int. Cl.² .................................... C07C 31/18
[58] Field of Search .............. 260/635 C; 252/455 R

[56] References Cited
UNITED STATES PATENTS

| | | | |
|---|---|---|---|
| 2,868,847 | 1/1959 | Boyers | 260/635 C |
| 3,055,840 | 9/1962 | Koch | 260/635 C |
| 3,779,946 | 12/1973 | Dorn et al. | 260/455 R X |

*Primary Examiner*—James O. Thomas, Jr.
*Assistant Examiner*—G. Breitenstein

[57] ABSTRACT

Process for the conversion of carbohydrates to polyhydric alcohols. Carbohydrates, such as glucose and cornstarch hydrolyzate, are converted to polyhydric alcohols by hydrogenation at high pressure in the presence of a catalyst comprising ruthenium on a crystalline aluminosilicate clay. The clay is preferably acid treated and calcined prior to impregnation with ruthenium. Clays containing a major proportion of montmorillonite are preferred.

9 Claims, No Drawings

POLYHYDRIC ALCOHOL PRODUCTION USING RU ON CLAY SUPPORTS

BACKGROUND OF THE INVENTION

This invention relates to processes for the conversion of carbohydrates to polyhydric alcohols. More particularly, this invention relates to processes for the production of polyhydric alcohols from carbohydrates using an improved supported ruthenium catalyst.

The term "carbohydrate" as used throughout the specification and claims includes monosaccharides and polysaccharides. This term includes both pure compounds, such as glucose and sucrose, and mixtures such as cornstarch hydrolyzate, which is a hydrolysis product of cornstarch containing glucose (dextrose) and oligomers thereof.

The term "polysaccharide" as used in the specification and claims includes those saccharides containing more than one monosaccharide unit. This term encompasses disaccharides and other saccharides containing a small number of monosaccharide units, which are commonly known as oligosaccharides.

The term "conversion" as used herein refers to hydrogenation when applied to monosaccharides and to a combination of hydrogenation and hydrolysis when applied to polysaccharides.

Catalytic processes may be broadly divided into processes using heterogeneous catalysts and those using homogeneous catalysts. Heterogeneous catalysts are those which are insoluble in the reaction medium, and are typically solid materials. Homogeneous catalysts are those which are soluble in the reaction medium, and are typically liquid. This invention is concerned with processes using a heterogeneous catalyst.

The conversion of carbohydrates to polyhydric alcohols using ruthenium on a solid carrier is known. U.S. Pat. No. 2,868,847 discloses the use of ruthenium on an inert catalyst support such as carbon, alumina, silica, or kieselguhr as a catalyst for the catalytic hydrogenation of saccharides such as dextrose, levulose, sucrose, maltose, and lactose. Starting materials include monosaccharides, e.g. dextrose and levulose, and disaccharides, e.g. sucrose, lactose, and maltose. Dextrose was hydrogenated to sorbitol and sucrose and lactose were hydrolyzed and hydrogenated to hexitols. However, maltose, a disaccharide containing two glucose units, was more easily converted to maltitol, a $C_{12}$ alcohol, according to the patent.

U.S. Pat. No. 3,055,840 discloses the hydrogenation of various carbonyl compounds, including glucose (which yields sorbitol or hydrogenation), using a promoted ruthenium catalyst on a solid carrier. Various solid carriers including carbon, silica gel, alumina, kieselguhr, and titanium dioxide, are disclosed.

The hydrogenation of monosaccharides using a supported ruthenium, palladium, platinum, or nickel catalyst (activated carbon was used as the support in all experimental work) is discussed in an article by N. A. Vasyunina et al., "Catalytic Properties of Ruthenium in Monosaccharides Hydrogenation Reaction", in *Izvestiya Akademii Nauk SSR Khimicheskaya Seriya* 4; 848–854 (1969). Ruthenium was found to have higher activity than the other three catalysts.

A two-stage process for hydrogenation of ligneous and other plant material such as wood sawdust is disclosed in *Izv. Akad.Nauk. SSR, Otd. Khim.* 8; 1522–1523 (1960). The process consists of a first stage hydrolytic hydrogenation of polysaccharides in an acid medium, followed by a second stage hydrogenation of the lignin in an alkaline medium, using a ruthenium catalyst in both stages. In a specific embodiment, pine sawdust is treated using an aqueous phosphoric acid medium and a ruthenium on carbon catalyst. The first stage reaction product is filtered to separate the liquid medium from the crystals obtained from the first stage filtrate.

In our co-pending application Ser. No. 498,969, filed Aug. 9, 1974, and Ser. No. 520,926, filed Nov. 5, 1974, which is a continuation-in-part of Ser. No. 498,969, there is disclosed a process for the conversion of carbohydrates such as cornstarch hydrolyzate and glucose to the corresponding polyhydric alcohol (or alcohols) using a ruthenium zeolite catalyst and preferably ruthenium on a type Y zeolite. High yields of sorbitol with excellent selectivity are obtained, although there is some difference in selectivity between different Y type zeolites. Furthermore, the ruthenium zeolite catalysts are easily regenerated with aqueous acid. The zeolites used for this purpose are synthetic crystalline aluminosilicates which have a well-defined cage structure that provides openings or pores of uniform size, as is well known. The principal disadvantages of the ruthenium zeolite catalysts are that the zeolites are expensive and available from relatively few sources of supply.

Various nickel catalysts for conversion of carbohydrates to polyhydric alcohols are also known. U.S. Pat. Nos. 3,538,019 and 3,670,035 and the references cited therein are examples of such catalysts. The supported nickel catalysts described in U.S. Pat. Nos. 3,538,019 and 3,670,035 (which is a division of U.S. Pat. No. 3,538,019) have high activity for the conversion of both monosaccharides and polysaccharides, including carbohydrate mixtures such as cornstarch hydrolyzate, with high selectivity to sorbitol when either cornstarch hydrolyzate or dextrose is used as the starting material. Carbon, diatomaceous earth, and kieselguhr are disclosed as carriers. This represents a significant improvement over the process and catalyst of U.S. Pat. No. 2,868,847, since the relatively inexpensive cornstarch hydrolyzate, or other commercially available carbohydrate mixtures, can be used as the starting material in place of the much more expensive pure sugars. A disadvantage of the catalyst in U.S. Pat. Nos. 3,538,019 and 3,670,035 is that the catalyst cannot be regenerated; when reactivation is required, it is necessary to remove the active catalyst material from the support by chemical means and then to redeposit the catalyst metal on the support.

SUMMARY AND OBJECTS

An object of this invention is to provide an improved process for the preparation of polyhydric alcohols from carbohydrates.

A further object is to provide a process for the conversion of carbohydrates to polyhydric alcohols using an improved ruthenium catalyst.

These and other objects will be apparent from the specification which follows.

According to the present invention, a polyhydric alcohol is produced from a carbohydrate by contacting said carbohydrate in an aqueous medium with hydrogen at elevated temperature and pressure in the presence of a catalyst comprising ruthenium on a crystalline aluminosilicate clay.

DESCRIPTION OF THE PREFERRED EMBODIMENT

Excellent yields of desired polyhydric alcohols, with minimal quantities of unconverted sugar and by-products, are obtained by using a ruthenium on clay catalyst as will be described below. These results are obtained even when relatively inexpensive starting materials, such as cornstarch hydrolyzate, are used. Carbohydrate starting materials and process conditions specified herein are for the most part conventional.

CATALYSTS

The catalysts used in the process of this invention comprise ruthenium on a crystalline aluminosilicate clay. The catalysts contain from about 0.1% to about 5%, preferably from about 0.5% to about 3% by weight of ruthenium, based on total catalyst weight. The ruthenium is present as the free metal finely dispersed on the surfaces of the clay, which serves as a support or carrier.

The clay minerals which are used in preparing the catalysts of this invention are hydrated crystalline aluminosilicates which have sheet or layer structures and which have base exchange capacity. These clays characteristically have a crystal structure which includes one or more tetrahedral silica layers and one or more octahedral alumina layers, with a variable amount of water and metal cations such as sodium, magnesium and calcium associated with the crystal lattice in cation or base exchange relationship. These layers are essentially two-dimensional sheet-like structures. Part of the silicon in the tetrahedral layer may be replaced by aluminum, and part of the aluminum may be replaced by other metals such as magnesium.

The clay supports for this invention should be essentially free of heavy metals, especially iron, or should have a low content of these metals. In general, clays which are suitable for use as catalysts for petroleum cracking or other petroleum processing operations are suitable as supports for the catalysts of this invention.

A preferred clay mineral is bentonite, which contains a major proportion of montmorillonite. (Bentonite is 90% montmorillonite, according to R. K. Iler, "The Colloid Chemistry of Silica and Silicates", Cornell University Press, Ithaca, N.Y., 1955, page 191.) Montmorillonite has an octahedral sheet or layer of alumina in which there may be some replacement of Al by Mg, sandwiched between two tetrahedral silica sheets in which part of the Si is replaced by Al. Montmorillonite has a nominal formula $Al_2O_3 \cdot 4SiO_2 \cdot H_2O + x\ H_2O$. Montmorillonite has a high base exchange capacity.

Another suitable clay mineral is synthetic mica montmorillonite (SMM), a synthetic clay-like aluminosilicate that is generally similar to muscovite mica. SMM is described in a paper by A. C. Wright et al. in *Journal of Catalysis* 25, 65–80 (1972). Basically, SMM has an octahedral alumina layer sandwiched between two tetrahedral silica layers, with partial substitution of Al for Si in the tetrahedral layers. SMM has base exchange capacity; the ammonium ion is the predominant exchangeable ion in uncalcined SMM.

Other clay minerals having a sheet-like structure, such as kaolinite, can also be used in preparing the catalysts of this invention. The base exchange capacity of kaolinite is significantly lower than that of montmorillonite, but is sufficient for the purposes of this invention. Clay minerals having a high base exchange capacity are in general preferred, however.

The clays are preferably activated prior to impregnation with ruthenium in order to increase the surface area and hence the catalyst activity. The preferred activation procedure for most clays is acid treatment followed by calcination.

Acid treatment and calcination of clays are known procedures in the art for improving catalyst activity, and acid treatment and calcination conditions known in the art can be used in preparing the instant catalyst. The raw clay can be treated directly with an aqueous mineral acid, such as hydrochloric or sulfuric acid; this differs from the treatment of alkali metal-containing zeolites, which must be converted by ion exchange to the ammonium form and then calcined, instead of being treated directly with acid. Acid treatment and calcination greatly increases the surface area of the clay; raw clays generally have too low a surface area to be suitable as catalyst supports, while acid treated clays typically have BET surface areas greater than 100 square meters per gram and most often greater than 150 square meters per gram, which are very desirable for catalyst use. Also acid treatment reduces iron content and removes alkali metal ions such as sodium, which are detrimental to catalyst activity. Magnesium and part of the aluminum present are also removed by acid treatment, so that an acid treated clay will have a higher silica/alumina ratio than the raw clay from which it was prepared. Acid treated clays also have an appreciable number of hydrogen ion sites which serves to catalyze the hydrolysis of polysaccharides in the carbohydrate starting material to monosaccharides.

Clay minerals which have a substantial quantity of exchangeable ammonium ions, such as SMM, can be activated by calcination alone. Calcination decomposes the ammonium ions into hydrogen ions, which provides acid sites. Activated SMM typically has a BET surface area of about 135–160 $m^2/g.$, the area depending largely on the temperature of activation.

Ruthenium can be deposited on the clay surfaces by ion exchange of the activated clay with an aqueous solution of a simple ruthenium salt, such as ruthenium trichloride, followed by reduction of the ruthenium to the metallic state. Better results are obtained with a simple ruthenium salt than with a complex ruthenium salt such as a ruthenium ammine salt. Ion exchange may be accomplished by known techniques, e.g., suspending the clay in the aqueous ruthenium salt solution at an elevated temperature and for a time sufficient to effect ion exchange, separating the ruthenium-impregnated clay particles from the solution by conventional means such as filtration, and drying the impregnated clay. This gives the unreduced form of the catalyst, in which the ruthenium is present as a trivalent cation. The ruthenium can then be reduced to the metallic state, either prior to being placed into service, or in situ during the first cycle of operation. The latter is preferred, since it requires fewer catalyst preparation steps and is therefore a lower cost operation. When the ruthenium is reduced in situ, the dried catalyst, containing ruthenium in the trivalent state, is suspended in an aqueous carbohydrate reaction medium; reduction of the ruthenium with hydrogen occurrs simultaneously with hydrogenation of the carbohydrate during the first cycle of operation. When the ruthenium is reduced prior to placing the catalyst into service, such reduction can be carried out either in the dry state, preferably at a temperature of about 100° to 200°C., or in an aqueous solution or slurry at elevated temperature (preferably about 100°–200°C.) and pressure, using hydrogen as the reducing agent in either case.

The presence of large quantities of sodium in the catalyst is detrimental to catalytic activity when the starting carbohydrate is a polysaccharide-containing material such as cornstarch hydrolyzate. The alkali metal content in that case is preferably not more than about 1% of total catalyst weight. The presence of ammonia (in the form of ammonium ions) in the catalyst likewise appears to be deleterious. Catalysts having an alkali metal content in excess of about 1% exert a buffering action on the reaction medium, and make it difficult or impossible to maintain the pH of the reaction medium sufficiently low to achieve complete hydrolysis of the polysaccharides present. The alkali metal and ammonia contents of the support prior to impregnation with ruthenium determine the final alkali metal and ammonia contents of the catalyst; therefore, clays having low alkali metal and ammonia contents should be used in preparing catalysts to be used with polysaccharide-containing carbohydrates. The alkali metal content of the catalyst is not important when the starting carbohydrate is a monosaccharide (e.g., glucose) or a mixture of monosaccharides. The presence of metal ions other than alkali metal ions in a catalyst is not harmful, provided the catalyst contains sufficient hydrogen ions to give the reaction medium the required acidity for hydrolysis of polysaccharides when the starting carbohydrate is a polysaccharide-containing material.

Amorphous supports, such as amorphous silica, alumina, or silica-alumina, are not suitable in the present process. A ruthenium on amorphous silica-alumina catalyst was found to give excessive quantities of by-products when used for the catalytic conversion of cornstarch hydrolyzate to sorbitol.

STARTING MATERIAL

Both monosaccharides and polysaccharides can be converted into polyhydric alcohols according to the present invention. Therefore, the carbohydrate starting material can be a monosaccharide or mixture thereof, or a polysaccharide-containing material. The latter term encompasses disaccharides and mixtures thereof, as well as carbohydrates comprising both a monosaccharide (or monosaccharides) and a polysaccharide or polysaccharides. The starting materials for the present process are known in the art as starting materials for the production of polyhydric alcohols by catalytic hydrogenation in the case of monosaccharides, or hydrolysis and hydrogenation in the case of polysaccharides.

Glucose is the most important monosaccharide starting material in the process of this invention. Illustrative examples of other monosaccharide starting materials include fructose, galactose, mannose, arabinose, ribose, and xylose. The pentoses and hexoses are the most important monosaccharides; more broadly, monosaccharides containing at least four (usually four to seven) carbon atoms can be hydrogenated to polyhydric alcohols according to this invention. Both aldoses (i.e., compounds having a terminal aldehyde or —CHO group) and ketoses (i.e., compounds having a keto or >CO group) can be treated.

Disaccharides which can be converted into polyhydric alcohols according to the present process include sucrose, maltose, lactose, cellobiose, and melibiose. Raffinose is a suitable trisaccharide starting material.

Other polysaccharide-containing starting materials include starch and starch decomposition products such as dextrin, glucose syrup, cellulose hydrolyzates, and starch hydrolyzates, e.g., cornstarch hydrolyzate. Preferred polysaccharide-containing starting materials are those which are readily hydrolyzable to monosaccharides, that is, those which can be hydrolyzed to monosaccharides under dilute acid conditions such as those used in the process of this invention, and which yield a single monosaccharide, preferably glucose, on hydrolysis.

Cornstarch hydrolyzate is a particularly preferred starting material in the present process because of its low cost. Other starch hydrolyzates are similar in composition to cornstarch hydrolyzate and can also be used with good results. Cornstarch hydrolyzate is a by-product of the hydrolysis of cornstarch to glucose. The hydrolyzate as produced contains some impurities, including electrolytes, which are detrimental in the present process; these impurities can be removed by treatment with a combination of a cation exchange resin and an anion exchange resin. The cation exchange resin can be either a strongly acid or weakly acid resin in the hydrogen form. The anion exchange resin is a weakly basic resin in the hydroxyl form; a strongly basic resin should not be used since this causes isomerization of some of the glucose present. The purified cornstarch hydrolyzate, which is used as a starting material for the present process, consists essentially of glucose (D-glucose or dextrose) and polymers thereof (primarily low molecular weight polymers or oligosaccharides, e.g., di-, tri-, and tetrasaccharides) which are composed entirely of glucose units and which, therefore, yield glucose as the only monosaccharide on hydrolysis. An outstanding feature of the present invention is that inexpensive and readily available carbohydrates such as cornstarch hydrolyzate can be used as starting materials with good yields of the desired polyhydric alcohol or alcohols (sorbitol when a starch hydrolyzate is the starting material) and with minimal quantities of by-products and sugars in the reaction product.

High molecular weight polysaccharides, such as cellulose and insoluble starch (e.g., cornstarch) can be used as starting materials but generally require more severe conditions of hydrolysis than those contemplated in the present invention. These materials are more advantageously partially hydrolyzed according to the methods known in the art with the formation of a hydrolyzate such as starch or cellulose hydrolyzate.

Monosaccharides containing an aldehyde group (i.e., aldoses) are hydrogenated almost exclusively by the process of this invention to a polyhydric alcohol having the same number of carbon atoms and the same space configuration of hydroxyl groups as the starting monosaccharide, but with a hydroxyl group in place of the carbonyl group of the starting material. Glucose, for example, is hydrogenated almost exclusively to sorbitol. (The presence of isomers such as mannitol and iditol is probably due to isomerization of sorbitol.) Monosaccharides containing a keto group in the molecule (i.e., ketoses) are hydrogenated to a mixture of two different isomeric polyhydric alcohols. Both polyhydric alcohols contain the same number of carbon atoms and the same configuration of hydroxyl groups (other than the hydroxyl group formed by reduction of the keto group) as the starting compound. Fructose, for example, has a keto group at the second carbon atom and is hydrogenated to approximately equal amounts of sorbitol and mannitol. Invert sugar, which consists of equimolar quantities of glucose and fructose, is hydrogenated to a reaction product containing approximately three mols of sorbitol for each mol of mannitol.

Polysaccharides are hydrolyzed to their basic monosaccharide (or monosaccharides) whose aldehyde or ketone groups are then hydrogenated to hydroxyl groups to produce the desired polyhydric alcohol (or alcohols) of the monosaccharide. Those polysaccharides having free aldehyde or ketone groups in their molecular structure before they are subjected to the process of this invention may have these groups hydrogenated at the same time the molecule is hydrolyzed. At any rate, both hydrolysis and hydrogenation reactions appear to take place simultaneously when polysaccharides are subjected to the process of the invention and the reaction results in the desired polyhydric alcohol (or alcohols) of the basic structural monosaccharides. Polysaccharides composed of different monosaccharide units are hydrolyzed and hydrogenated to the polyhydric alcohols of the respective monosaccharides. When sucrose (whose basic structural monosaccharides are glucose and fructose) is hydrolyzed, and hydrogenated, the resulting reaction product is a sorbitol-mannitol mixture in the molar ratio of approximately 3/1. Cornstarch hydrolyzate (in which the polysaccharides consist of glucose units) yields sorbitol, with isomers thereof (e.g., mannitol and iditol) present only in small by-product amounts.

REACTION CONDITIONS

The present process uses an aqueous reaction medium. The carbohydrate or carbohydrates to be subjected to the process of this invention are dissolved in water at the appropriate concentration for the conversion reaction. Concentrations of carbohydrates from about 20% to about 80% by weight are usually employed for the reaction. Carbohydrate concentrations in the range of about 40% to about 70% by weight react particularly smoothly in the reaction and such concentration are, therefore, the more preferred for this invention. It is not necessary for the carbohydrates to form true solutions with the water, as suspensions and colloidal solutions of carbohydrates readily react.

The amount of catalyst to be used in the process of this invention may vary over a wide range and will depend upon the particular catalyst, carbohydrate, temperature, and pressure which are employed in the process. Polysaccharides tend to require a higher level of catalysts than the monosaccharides. In general, catalyst concentrations required when using the catalysts herein tend to be appreciably lower than those used for nickel catalysts. Catalyst concentrations ranging from about 0.01% to about 0.1%, preferably from about 0.02% to about 0.05% by weight of total ruthenium based on the weight of carbohydrate are suitable.

The reaction can be carried out either in one stage or two stages. More than two stages can be utilized but this is seldom necessary or advantageous. Excellent results can be obtained with one stage when a monosaccharide or mixture of monosaccharides is treated. However, the two-stage operation is preferred when a polysaccharide-containing carbohydrate, such as cornstarch hydrolyzate, is used as the starting material, because two-stage operation results in better conversion to the desired polyhydric alcohol or alcohols with smaller amounts of impurities. The second stage in a two-stage operation is generally conducted at a higher temperature than the first stage. Reaction pressures are typically about the same in both stages. The advantage of two-stage treatment is that more effective hydrolysis of polysaccharides is achieved in this manner. When a starting material containing both a monosaccharide and polysaccharides (e.g., cornstarch hydrolyzate) is used, it appears that hydrogenation of the monosaccharide content occurs in the first stage, while hydrolysis of the polysaccharides and hydrogenation of the monosaccharides thus produced occurs primarily in the second stage.

The pressures and temperature employed in the process of this invention may vary over wide limits. The reaction may be carried out at temperatures from about 100° to about 200°C. and at hydrogen pressures of at least about 100 psig. The preferred ranges of pressure and temperature are from about 1000 psig. to about 3000 psig. and from about 140° to about 180°C. respectively. Generally, lower temperatures are preferred for the hydrogenation of monosaccharides than for the conversion of polysaccharide-containing starting materials. Monosaccharides are advantageously hydrogenated at about 100° to about 160°C. Polysaccharide-containing starting materials, on the other hand, require a temperature of at least about 170°C. during at least a portion of the reaction period. When a polysaccharide-containing carbohydrate such as cornstarch hydrolyzate is treated in a two-stage process according to this invention, the preferred firststage temperatures are in the range of about 100° to about 175°C., preferably about 120° to about 160°C., and second-stage temperatures range from about 170°C. to about 200°C., preferably about 175° to about 180°C. It is to be understood that higher and lower pressures and temperatures than those described above may be used when deemed necessary or desirable.

The time of reaction will depend upon the specific carbohydrate or carbohydrates being acted upon, the specific hydrogenation catalyst used, pressure, temperature, and the concentration of the carbohydrate. Generally, the reaction time is in the range of about 0.25 hour to about 3 hours. Polysaccharide-containing starting materials usually require longer reaction times than monosaccharides. The reaction time for hydrogenation of a monosaccharide or monosaccharides is at least about ¼ hour and is preferably from about 0.5 to about 1 hour. The hydrogenation of a monosaccharide is ordinarily complete in an hour or less. Reaction times less than about 0.5 hour ordinarily require higher catalyst concentrations than times of 0.5 hour or longer. The reaction time for conversion of polysaccharide-containing carbohydrates is at least about 0.5 hour, preferably from about 1 to about 3 hours. Reaction times less than about 1 hour usually require higher catalyst concentrations than longer reaction times. In a two-stage treatment of a polysaccharide-containing carbohydrate, each stage typically lasts about 0.5 to about 1.5 hours. In any case, the reaction should be continued until hydrolysis and hydrogenation have been completed.

Reaction times substantially longer than those required should be avoided whenever a reaction temperature above about 160°C. is used. The catalysts used herein catalyze the isomerization of sorbitol at temperatures about 160°C., so that mannitol and in some cases iditol will be produced if contact between the catalyst and the reaction medium is continued for an unnecessarily long time.

The pH of the reaction medium is at least about 2.5 and preferably at least about 3.0. At pH values below about 2.5, and to a lesser extent at values below about 3.0, the catalyst support tends to lose part of its crystallinity with consequent deterioration due to acid attack. The rate of deterioration increases as the pH is decreased. Also, it appears that the formation of certain by-products, notably hexitans such as 1,4-sorbitan, is increased as the pH value falls below about 3.

When the starting material is a polysaccharide-containing material such as cornstarch hydrolyzate or other starch hydrolyzate, the pH of the reaction medium should be in the range of about 2.5 to about 4.5, preferably from about 3.0 to about 4.0. It appears more important to maintain the pH range during the latter portion of the reaction (e.g., during the second stage) than during the first portion. At reaction product pH values above about 4.5 and to a lesser extent at values above about 4.0, hydrolysis of polysaccharides is incomplete and sugars are present in the reaction product. The use of a catalyst containing no more than about 1% alkali metal by weight is important in achieving the desired pH. An acid can be added to the reaction medium, either at the outset or during the reaction, e.g., between the first and second stages (the latter is ordinarily preferred) for pH control. Common mineral acids, such as sulfuric acid and phosphoric acid, give good results. Hydrochloride acid can also be used but is harmful to stainless steel equipment.

Monosaccharides such as glucose can be hydrogenated over a much wider pH range than polysaccharide-containing carbohydrates. Both acidic and neutral media (e.g., media having a pH up to about 7.5) are suitable for hydrogenation of monosaccharides.

The reactants may be added to the reaction chamber in any suitable manner or in any suitable order. It is preferred to add the catalyst to the aqueous solution or suspension of the carbohydrate and then add the hydrogen under pressure and commence heating the mixture to the desired temperature.

The reaction is carried out in any suitable type of apparatus which enable intimate contact of the reactants and control of the operating conditions and which is resistant to the high pressures involved. The process may be carried out in batch, semi-continuous, or continuous operation. Batch operation in a conventional autoclave gives excellent results.

Upon completion of the reaction, the catalyst is removed by filtration or decantation and the polyhydric alcohol may be separated from the filtrate by any suitable means, such as filtration, washing, crystallization, solvent extraction, or evaporation. Any electrolytes which may be present in the filtrate may be removed prior to recovery of the polyhydric alcohols by passage through a mixed ion exchange bed which contains both a cation exchange resin and an anion exchange resin.

CATALYST REGENERATION

The catalyst is readily regenerated by washing with a dilute aqueous mineral acid, such as sulfuric acid, hydrochloric acid, or phosphoric acid at room temperature. Acid concentrations ranging from about 0.01 N to about 0.5 N can be used. While acid concentrations higher than 0.5 N effectively regenerate the catalyst, they also cause partial loss of crystallinity of the support (due to dissolution of part of the alumina) and therefore should be avoided. The acid wash is preferably followed with a water wash. When the catalyst is separated from the reaction product by filtration, the wet catalyst may be acid washed on the filter. The catalyst should be acid washed after each use when a starch or cellulose hydrolyzate is treated; failure to acid wash usually results in appreciably reduced activity during the next use. Less frequent regeneration will suffice when the starting material is a monosaccharide. A complete operating cycle includes reaction of a carbohydrate as above described followed by catalyst regeneration.

ADVANTAGES

A major advantage of the catalysts used herein is that they give good yields of desired polyhydric alcohol with minimal quantities of undesired polyhydric alcohols, other impurities, and unconverted sugars in the reaction product, even when inexpensive and readily available polysaccharide-containing carbohydrates such as cornstarch hydrolyzate are used as starting materials. Good selectivity to sorbitol is obtained when cornstarch hydrolyzate is the starting carbohydrate.

Another advantage of the ruthenium on clay catalysts herein is that these catalysts have good activity. Because of good catalyst activity, reaction time tends to be somewhat shorter with the catalyst of this invention than with most other supported ruthenium catalysts or commonly used nickel catalysts, particularly when cornstarch hydrolyzate is the starting material.

Another important advantage of the catalysts herein over ruthenium catalysts on certain other supports, such as carbon, is that the catalysts herein are physically more rugged.

A major advantage of the catalysts used in the present invention over commonly used nickel catalysts is that they can be regenerated by a simple acid wash, and do not require removal from the carrier (i.e., by dissolution) or redeposition on the carrier.

Another advantage of the catalysts herein is that they use a comparatively inexpensive and readily available support.

This invention will now be described further with respect to the following examples.

EXAMPLE 1

This example describes the production of sorbitol from cornstarch hydrolyzate using, as the catalyst, 1% by weight ruthenium on an acid-treated calcined montmorillonite clay.

The cornstarch hydrolyzate used in these examples is a by-product obtained from the hydrolysis of cornstarch to glucose and purified by treatment with a cation exchange resin and an anion exchange resin. The purified cornstarch hydrolyzate consists essentially of glucose, oligomers thereof, and water. A typical analysis, by weight on the dry basis, is as follows: glucose, 63%; disaccharides, 17%; trisaccharides, 4%; tetrasaccharides, 3%; and higher polysaccharides, 12%. The analysis varies somewhat from batch to batch.

The catalyst support used in this example was an acid-treated calcined montmorillonite clay sold under the designation "K-10" by Chemetron Corporation. This material is a powder which typically contains about 64.7% by weight silica and 19.3% by weight alumina, and which typically has a pH of about 3.5 in a 1:10 (by weight) clay/water slurry, a bulk density of about 373 g/liter, a specific gravity of about 2.4–2.5, and a surface area of 268 m²/g.

To prepare the catalyst, a slurry of 20 grams of "K-10" montmorillonite clay in 300 ml. of distilled water was added to a solution of 0.5 grams of ruthenium chloride (40% Ru) in 200 ml. of distilled water in a 1-liter beaker. The resulting slurry was heated on an electric hot plate with magnetic stirring at 70°–80°C. for 1 hour. During this time the color of the slurry changed from gray-greenish to gray. The slurry was filtered and washed with three 50-ml. portions of distilled water. Analysis of the filtrate showed less than 1 ppm Ru. The ruthenium-exchanged catalyst was dried in an oven for 12 hours at 100°C. and was used without reduction.

Five operating cycles were carried out in which cornstarch hydrolyzate was converted to sorbitol using the catalyst described above, followed by acid regeneration of the catalyst.

An aqueous slurry was prepared by slurrying 3.0 grams of the above-described catalyst in an aqueous solution of cornstarch hydrolyzate containing 100 grams of sugar solids and having a solids concentration of about 68–70% by weight. The pH of the slurry (which will be called "initial pH") was determined and the slurry was charged in an inert atmosphere to a 1-liter autoclave equipped with a stirrer. Fresh catalyst was used in the first cycle; dried, reused catalyst recovered from the previous cycle plus enough makeup catalyst to give a total catalyst weight of 3.0 grams was used in the subsequent cycles. The ruthenium content of the catalyst was reduced from the trivalent to the metallic form during the first cycle.

Conversion of cornstarch hydrolyzate to sorbitol was carried out in two stages, at temperatures of 160°C., and 175°C., respectively. The autoclave was purged with nitrogen and hydrogen, pressured with hydrogen to about 1500–1550 psig. at room temperature, and heated to 160°C. The pressure rose during heating to about 1900–2000 psig. (There were some variations from cycle to cycle.) The temperature was maintained at 160°C. for 30–47 minutes (exact times for each cycle are indicated in Table I below) during the first reaction stage. Some pressure drop (typically about 120–180 psig.) occurred due to hydrogen consumption. Then 3 ml. of 0.36 N sulfuric acid, diluted to 15 ml. with distilled water, was added to the autoclave by hydrogen displacement. (This raised the pressure to about 2000 psig. at 160°C.) The autoclave contents were heated to 175°C. and maintained at this temperature for 30 minutes. A slight pressure drop (typically about 30 psig.) occurred during the second stage of each cycle.

The autoclave contents were cooled to room temperature, discharged from the autoclave, filtered, ion-exchanged through a mixed bed of ion-exchange resins, concentrated to about 70% solids and analyzed. The pH of the reaction product (final pH) was determined before filtration.

The catalyst on the Buechner funnel was regenerated by washing with three 50-ml. portions of dilute aqueous 0.36 N sulfuric acid.

Operating conditions and product analyses (in percent by weight on the dry basis) for the second, third and fourth cycles are given for each cycle in TABLE I.

TABLE I

| Cycle | 2 | 3 | 4 |
|---|---|---|---|
| Catalyst re-use | 1 | 2 | 3 |
| Initial pH | 3.3 | 3.2 | 3.2 |
| Final pH | 3.0 | 2.9 | 2.9 |
| First stage | | | |
| Temp., °C. | 160° | 160° | 160° |
| Time, min. | 35 | 40 | 45 |
| Second stage | | | |
| Temp., °C. | 175° | 175° | 175° |
| Time, min. | 30 | 30 | 30 |
| Product: | | | |
| Sorbitol | 91.7 | 90.7 | 92.7 |
| Mannitol | 1.92 | 2.27 | 2.67 |
| Total non-sugar impurities | 5.73 | 6.24 | 5.04 |
| Reducing sugar | 0.04 | 0.09 | 0.22 |
| Total sugar | 0.07 | 0.15 | 0.30 |
| Sorbitol by difference | 94.2 | 93.6 | 94.7 |

The first cycle product was not analyzed in its entirety, since conversion to sorbitol tend to be less selective in the first cycle than in subsequent cycles.

The fifth cycle reaction product contained 1.95% by weight (dry basis) total sugar, of which 1.45% was reducing sugar. Reaction conditions in the fifth cycle were similar to those in the fourth cycle. The high reducing sugar value suggests incomplete hydrogenation of glucose present in the cornstarch hydrolyzate, which in turn suggests diminished catalyst activity.

The value, "sorbitol by difference" in Table I above (and in Tables II and III which follow) is determined by adding "total non-sugar impurities" and "total sugar" (which gives total impurities) and subtracting the sum from 100.

EXAMPLE 2

This example describes the production of sorbitol from cornstarch hydrolyzate using, as the catalyst, 1% by weight ruthenium on a montmorillonite clay in the hydrogen form, obtained by ion exchange of the starting clay with ammonium ions followed by calcination.

The montmorillonite clay ("K-10", Chemetron) was ion exchanged with aqueous ammonium nitrate, dried in a vacuum oven at 140°C. for 4 hours, calcined at 425°C. for 14 hours, and then ion exchanged with ruthenium chloride as described in Example 1. The ruthenium-exchanged clay was treated with a flowing stream of hydrogen at 150°C. for 30 minutes to reduce the ruthenium to the metallic state. Reduction was carried out prior to first use of the catalyst.

Seven operating cycles were carried out in which cornstarch hydrolyzate was converted to sorbitol using the catalyst described above, followed by regeneration of the catalyst with acid. Both conversion and regeneration were carried out according to the procedure described in Example 1, except for differences in the first and second stage conversion times as indicated in Table II below. Table II indicates operating conditions and product analyses in percentage by weight on the dry basis for the first, second, sixth, and seventh cycles.

TABLE II

| Cycle | 1 | 2 | 6 | 7 |
|---|---|---|---|---|
| Catalyst re-use | 0 | 1 | 5 | 6 |
| Initial pH | 3.6 | 3.3 | 3.2 | 3.2 |
| Final pH | 2.9 | 3.0 | 2.9 | 2.9 |
| First stage: | | | | |
| Temp., °C. | 160° | 160° | 160° | 160° |

TABLE II-continued

| Cycle | 1 | 2 | 6 | 7 |
|---|---|---|---|---|
| Time, min. | 45 | 65 | 60 | 65 |
| Second stage: | | | | |
| Temp., °C. | 175° | 175° | 175° | 175° |
| Time, min. | 30 | 30 | 30 | 30 |
| Product: | | | | |
| Sorbitol | 92.2 | 92.4 | 92.7 | |
| Mannitol | 1.61 | 2.30 | 1.88 | |
| Total non-sugar impurities | 3.79 | 5.18 | 4.76 | |
| Reducing sugar | 0.09 | 0.11 | 0.19 | 0.89 |
| Total sugar | 0.73 | 0.15 | 0.32 | 1.25 |
| Sorbitol by difference | 95.5 | 94.7 | 94.9 | |

Complete analyses of the third, fourth, and fifth cycles were not made because of the relatively high total sugar contents in the products of each of these cycles.

EXAMPLE 3

This example describes the production of sorbitol from cornstarch hydrolyzate using, as the catalyst, 1% by weight ruthenium on synthetic mica montmorillonite (SMM).

The synthetic mica montmorillonite used in this example was obtained from Baroid Division of NL Industries under the name BARASYM SMM. Ruthenium was incorporated by ion exchange using the procedure of Example 1. The trivalent ruthenium in the ruthenium-exchange SMM was reduced with a stream of hydrogen at 150°C. for 30 minutes.

Six operating cycles were carried out in which cornstarch hydrolyzate was converted to sorbitol using the catalyst described above, followed by acid regeneration of the catalyst. Both conversion and regeneration were carried out according to the procedure of Example 1, except for differences in first and second stage reaction times during conversion as indicated in Table III below. Table III indicates operating conditions and product analyses in percentage by weight on the dry basis for the first, fourth, fifth, and sixth cycles.

TABLE III

| Cycle | 1 | 4 | 5 | 6 |
|---|---|---|---|---|
| Catalyst re-use | 0 | 3 | 4 | 5 |
| Initial pH | 4.2 | 3.5 | 3.6 | 3.6 |
| Final pH | 3.6 | 3.0 | 3.4 | 3.2 |
| First stage: | | | | |
| Temp., °C. | 160° | 160° | 160° | 160° |
| Time, min. | 30 | 60 | 65 | 80 |
| Second stage: | | | | |
| Temp., °C. | 175° | 175° | 175° | 175° |
| Time, min. | 30 | 30 | 40 | 32 |
| Product: | | | | |
| Sorbitol | | 91.3 | 91.1 | 89.6 |
| Mannitol | | 2.35 | 2.75 | 3.19 |
| Total non-sugar impurities | | 5.76 | 5.77 | 5.86 |
| Reducing sugar | 0.19 | 0.21 | 0.24 | 0.67 |
| Total sugar | 0.70 | 0.28 | 0.42 | 0.95 |
| Sorbitol by difference | | 94.0 | 93.8 | 93.2 |

We claim:

1. A process for the production of a polyhydric alcohol or mixture thereof which comprises contacting an essentially water soluble polysaccharide-containing carbohydrate in aqueous medium with hydrogen at a temperature in the range of about 100° to about 200°C., a pressure of at least about 100 psig, and a pH in the range of about 2.5 to about 4.5, in the presence of a catalyst comprising ruthenium wherein the catalyst contains about 0.1% to about 5% by weight of ruthenium, based on the total catalyst weight, an acid activated crystalline aluminosilicate clay having base exchange capacity and having a layer structure comprising a plurality of sheet-like layers, said layers including at least one tetrahedral silica layer and at least one octahedral alumina layer.

2. A process according to claim 1 in which said clay is acid treated and calcined.

3. A process according to claim 1 in which said clay has high cation exchange capacity.

4. A process according to claim 1 in which said clay comprises a major proportion of montmorillonite.

5. A process according to claim 1 in which said carbohydrate is a hydrolyzate of starch of cellulose.

6. A process according to claim 5 in which said hydrolyzate is a starch hydrolyzate.

7. A process according to claim 1 in which the reaction time is at least about 0.5 hour.

8. A process according to claim 1 in which the reaction temperature is at least about 170°C during at least a portion of the reaction period.

9. A process according to claim 8 in which the reaction is carried out in two stages, the first stage being carried out at a temperature in the range of about 100° to about 175°C. and the second stage being carried out at a temperature of about 170° to about 200°C.

* * * * *